United States Patent [19]

van't Hooft et al.

[11] Patent Number: 4,969,863
[45] Date of Patent: Nov. 13, 1990

[54] ADAPTOR FOR REMOTE AFTER-LOADING APPARATUS FOR RADIOTHERAPY

[75] Inventors: Eric van't Hooft, Gezichtslaan 16, 3956 BB Leersum, Netherlands; Libbe van Zwol, Leersum, Netherlands

[73] Assignee: Eric van't Hooft, Leersum, Netherlands

[21] Appl. No.: 263,937

[22] Filed: Oct. 28, 1988

[51] Int. Cl.⁵ .............................................. A61N 5/00
[52] U.S. Cl. .......................................... 600/3; 600/7; 285/316
[58] Field of Search .................................... 600/1, 3–6, 600/7; 604/283, 905; 128/912; 285/319, 320, 316, 314

[56] References Cited

U.S. PATENT DOCUMENTS

| 2,429,202 | 10/1947 | Estill et al. | 285/316 |
| 2,784,987 | 3/1957 | Corcoran | 285/319 |
| 2,819,733 | 1/1958 | Maisch | 285/320 |
| 3,601,361 | 8/1971 | Hundhausen | 285/319 |
| 3,649,053 | 3/1972 | Synder, Jr. | 285/316 |
| 3,669,093 | 6/1972 | Sauerwein et al. | 600/7 |
| 4,828,296 | 5/1989 | Medvick | 285/316 |
| 4,881,937 | 11/1989 | van't Hooft et al. | 600/3 |
| 4,897,076 | 1/1990 | Puthawala et al. | 600/3 |

FOREIGN PATENT DOCUMENTS

| 0152124 | 8/1985 | European Pat. Off. | 600/7 |
| 0158630 | 10/1985 | European Pat. Off. | 600/7 |
| 3313857 | 10/1984 | Fed. Rep. of Germany | 600/7 |
| 3442762 | 6/1986 | Fed. Rep. of Germany | 600/7 |

Primary Examiner—Stephen C. Pellegrino
Assistant Examiner—Ralph Lewis
Attorney, Agent, or Firm—Griffin Branigan & Butler

[57] ABSTRACT

The adaptor for connecting a guide member in a remote after-loading apparatus for radiotherapy is provided. The adaptor comprises an outer barrel having an opened end, a connector end and a centrally extending aperture. A sleeve passes through the aperture of the barrel such that at least a first end of the sleeve is contained within the barrel. An elongated gripping means is disposed through the sleeve and extends beyond the ends of the sleeve. The gripping means has a gripping end and a receiving end, a gripping body extending between the ends, and a flange disposed on the gripping end with the diameter of the flange being greater than the diameter of the sleeve. A tapered outer surface extends from the flange to a distant portion of the gripping body. A uniform diameter tube bore is disposed through the gripping means and at least two slots pass through the flange and at least a portion of the gripping body. Those slots form at least two opposed gripping portions which are inwardly compressible when the flange and the gripping portions are in contact with the first end of the sleeve, so as to form a reduced diameter of the tube bore and thereby a closed position of the gripping portions. The gripping portions are sufficiently resilient so that when the flange and the gripping portions are disposed from the first end of the sleeve, the gripping portions form at least the same diameter as the tube bore and thereby an open position. Spring means are disposed between the gripping means in the sleeve for urging the flange of the gripping means toward the second end of the sleeve.

22 Claims, 2 Drawing Sheets

U.S. Patent    Nov. 13, 1990    Sheet 1 of 2    4,969,863
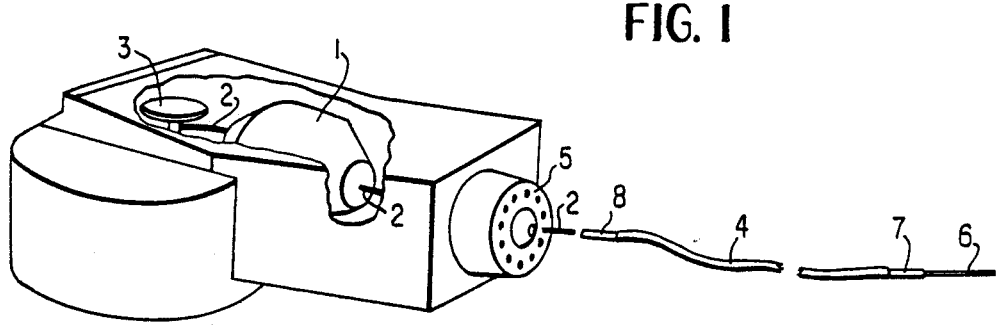
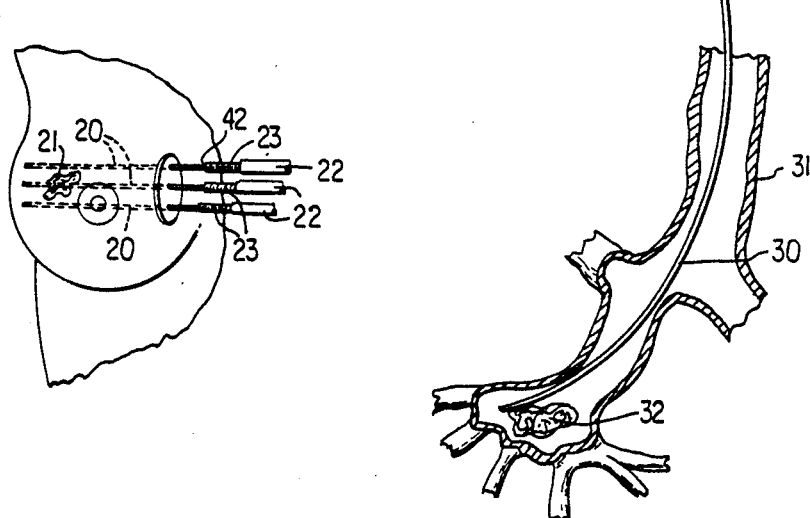
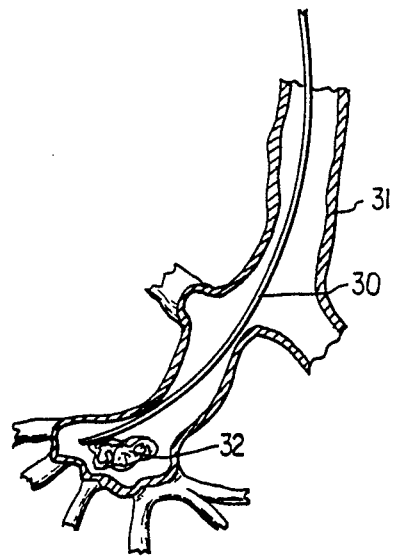
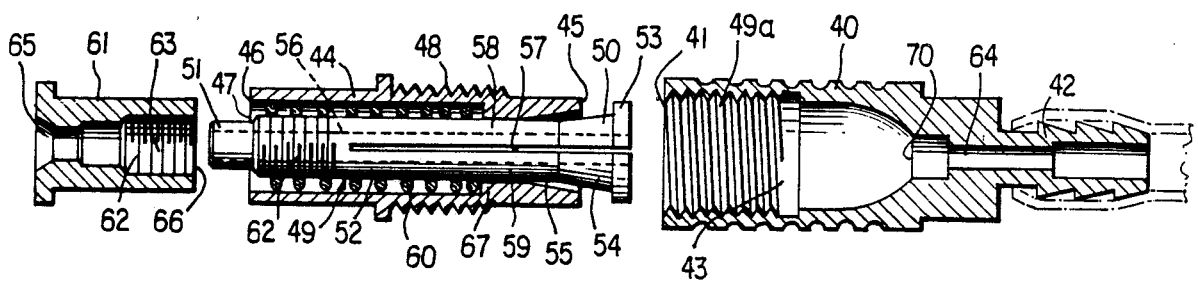
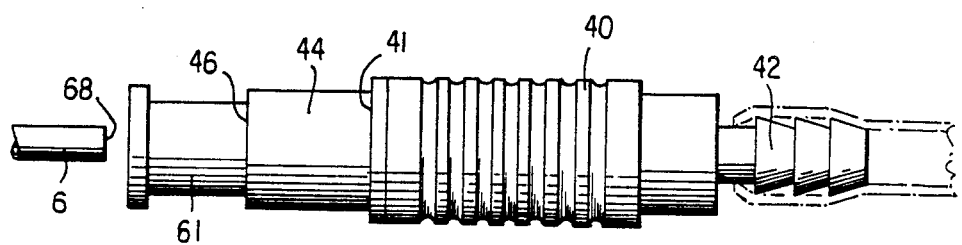

ADAPTOR FOR REMOTE AFTER-LOADING APPARATUS FOR RADIOTHERAPY

The present invention relates to an improvement in a remote after-loading apparatus for brachy therapy, e.g. interstitial, intracavitary and intralumenal radiotherapy, and more particularly, to adaptors for such apparatus.

BACKGROUND OF THE INVENTION

Brachy therapy has become of increased importance in the treatment of certain diseases, especially cancer, in that the radiotherapy can be administered to very localized human body areas, as opposed to broad beam radiotherapy. To achieve this localized radiotherapy, a radioactive source must be placed in close proximity to the tissue being treated, since the radioactive source effects only low levels of radiation at a significant distance from the source, while high levels of radiation are effected near the source, i.e. the application of the inverse square of the distance law. The application of the radiotherapy is normally achieved by guiding a radioactive source through at least one guide member, e.g. a position member or a tubular guide, until that source reaches the site of the tissue to be treated, e.g, cancerous tissue. A regimen of radiation is then administered according to a program defined for the particular cancerous tissue and that therapy is, usually, periodically repeated until effective control of the cancerous tissue is achieved.

However, since radiation is involved in the therapy, technicians who routinely administer the therapy to a number of patients would be unduly exposed to radiation in the conduct of those therapies if the technician were in close proximity to the patient being treated. To avoid such radiation hazard to the technician, apparatus has been developed for allowing the radiation source to be moved to the site of the radiotherapy while the technician is not in close proximity to the patients being treated, e.g. is not in the treatment room where the patient is being treated. Such apparatus is known in the art as remote afterloading apparatus for brachy therapy. When using such apparatus, a physician places a positioning member, e.g. a needle or canula, at the site where radiotherapy is to be effected. This positioning member in some applications may be attached to one end of a tubular guide and the tubular guide is attached at the other end thereof to a connection head of the remote afterloading apparatus. After such positioning and connections are made, a technician, from a remote location, e.g. another room, can cause the apparatus to drive a cable with a radioactive source attached thereto from a "safe", through the remote after-loading apparatus, the guide member, e.g. tubular guide, and into the positioning member for radiotherapy. Thus, a technician will not be in close proximity to the patients, e.g. will be in another room, while the radioactive source is out of the "safe" and while administering the therapy.

While apparatus of the above nature has been used for some time, a particular problem in connection therewith has been the adaptors for connecting the guide member, e.g. tubular guide, and/or the positioning member to the connection head of the remote afterloading apparatus or attaching the one to the other. For example, since the cable, with the radioactive source, must slide through the tubular guide, and the tubular guide is quite small, any kinking, compressed configuration, or the like of the flexible plastic tubular guide, caused by the adaptor, can cause the cable moving the radioactive source to bind therein, which results in a failure of moving the radioactive source to the correct site for effective radiotherapy. Thus, the adaptors have been a constant problem in the art. In addition, once the positioning member is in place in the patient, it is important to quickly and effectively connect the tubular guide to the positioning member or the positioning member to the connection head so as to minimize delay and discomfort to the patient.

In the past, such adaptors have taken the general form of metal tubes and the tubular guide or positioning member is slid (partially forced) thereover. However, in view of the very small diameters of the flexible, plastic tubular guides or positioning members, the time required for so attaching the same to a metal tube is inordinately long and in addition, distortion during attachment can cause uneven compression of the flexible, plastic tubular guide or positioning member which will result in the kinking, binding and the like of the cable with the radioactive source attached thereto. Thus, it would be of substantial advantage to the art to provide improved adaptors for connecting the tubular guide or positioning member to the connection head or to each other wherein the adaptors allow for quick and easy connections without the necessity of fitting to a metal tube or any other laborious attachments, such as screwing or unscrewing devises, and where such connections avoiding distortion or compression of the tubular guide or positioning member so as to avoid the kinking, binding and the like by the cable.

BRIEF DESCRIPTION OF THE INVENTION

Generally speaking, the necessary parts of a remote after-loading apparatus for brachy therapy comprises a radioactive source, a safe for the source (to avoid radiation exposure to technicians working with the apparatus), a source drive cable for driving the source from the safe to the site of the therapy, a guide member for guiding the cable to the site of the radiotherapy, a connection head for connecting the guide member to the source drive cable, a positioning member for positioning the source at the site of the radiotherapy and adaptors for connecting the guide member to the connection head and/or the positioning member. In this combination, the present invention involves an improvement in the adaptors for connecting the guide member to the connection head and/or the positioning member. The guide member may be in the form of, for example, a cannula disposed from the head to the site of radiotherapy, and thus the guide member includes the positioning member, or in the form of a tubular guide which is connected to a positioning member. For the sake of conciseness, the invention will be, mainly, described in regard to the embodiment which uses a tubular guide, but it is to be understood that the invention is fully applicable to both of these embodiments.

The adaptor comprises an outer barrel having an opened end and a connector end and having a centrally extending aperture therein. A sleeve having a first end and a second end and a passageway extending between said ends is disposed within the barrel such that at least the first end of the sleeve is contained within the barrel. An elongated gripping means is disposed through the sleeve passageway and extends beyond the ends of the sleeve. The gripping means has a gripping end and a receiving end, a gripping body extending from the gripping end to the receiving end, and a flange disposed on the gripping end such that the diameter of the flange is greater than the diameter of the sleeve passageway at the first end thereof. There is a tapered outer surface extending from the flange to a distant portion of the gripping body. A uniform diameter gripping means tube bore is disposed through the gripping means and at least two slots pass through the flange and the gripping body and extend from the flange to at least the distant portion of the gripping body. Those at least two slots form at least two opposed gripping portions of the gripping means and the gripping portions are inwardly compressible when the flange and the gripping portions are in contact with the first end of the sleeve, so as to form a reduced diameter of the tube bore and thereby a closed position of the gripping portions. The gripping portions are sufficiently resilient so that when the flange and the gripping portions are axially disposed from the first end of the sleeve, the gripping portions form at least the same diameter as the tube bore and thereby an open position. Spring means are disposed between the gripping means in the sleeve for urging the flange of the gripping means toward the second end of the sleeve.

With this arrangement the tubular guide (or the positioning member) may be moved into the receiving end of the gripping means, moved to engage the gripping portions in the closed position, moved so as to cause the gripping means to be moved against the spring means axially outwardly from the first end of the sleeve to a position where at least a portion of the tapered outer surface is spaced from the first end of the sleeve and the flange and the gripping portions are resiliently moved to the open position and allow passage of the tubular guide (or positioning member) therethrough. Upon ceasing the movement of the tubular guide (or positioning member), the spring means urges the gripping means axially inwardly in the sleeve so that a portion of the tapered outer surface contacts the first end of the sleeve and compresses the gripping portions to a locked position around the tubular guide (or positioning member).

By this arrangement, the tubular guide (or positioning member) may be very quickly inserted into the adaptor and locked in place by that insertion in such a manner that the tubular guide (or positioning member) is not substantially compressed, and thereby avoids kinking and binding and the like of the source drive cable.

BRIEF DESCRIPTION OF THE DRAWINGS

FIG. 1 is a diagrammatic view of the basic parts of a conventional remote after-loading apparatus for brachytherapy.

FIG. 2 is a diagrammatic illustration of positioning members positioned for treatment of breast cancer and showing the positioning members being connected via adaptors to tubular guides (one of the embodiments of the invention).

FIG. 3 is a diagrammatic illustration of a positioning member in position for treating lung cancer.

FIG. 4 is an exploded view, partly in cross section, of an embodiment of the adaptor of the present invention.

FIG. 5 is an assembled view of FIG. 4.

DETAILED DESCRIPTION OF THE INVENTION

Figure 6:
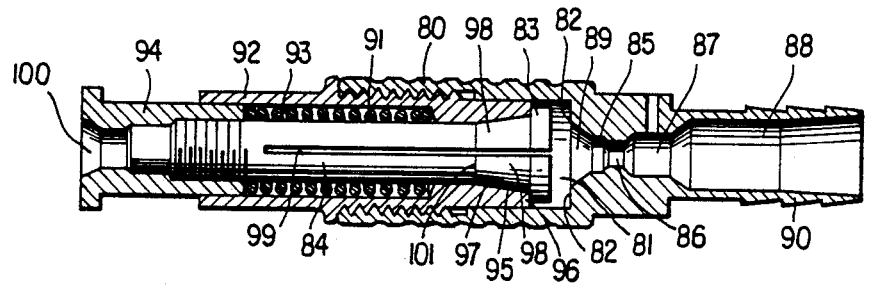
FIG. 6 is a view of a preferred embodiment of the present adaptor, which view is partially in cross section.

While remote after-loading apparatus for brachy therapy, e.g. intracavitary intralumenal and interstitial radiotherapy, is well known in the art (see for example applicant's U.S. Pat. Nos. 4,881,938 and 4,881,937 which are incorporated herein by reference), and need not be described in detail herein for sake of conciseness, for context purpose, a typical arrangement of such apparatus is shown in FIG. 1. The basic parts of a typical apparatus are as follows. A radioactive source (not shown in the drawings) is contained in a safe 1 which protects technicians from radiation while working with the apparatus. A source drive cable 2 is driven by a source drive mechanism 3. To position the radioactive source at the site of the therapy a guide member, e.g. a tubular guide 4 is as disposed so as to guide the drive cable 2 to the site of the radiotherapy. It should be understood in this regard that the patient being treated will be in proximity to the remote after-loading apparatus and may be conveniently sitting in a chair or lying on a bed, depending primarily upon the particular radiotherapy being administered. Thus, the tubular guide is necessary for guiding the drive cable 2 with the radioactive source from the safe to the site of treatment. A connection head 5 connects one or more of tubular guides 4 to one or more of source drive cables and these one or more connections are referred to as "channels." As noted above, for some applications, the positioning member may extend from the site to be treated to the connection head 5, and in this form the positioning member includes the guide member, but for sake of conciseness, the embodiment where the positioning member and the guide member are separate, i.e. utilizing a tubular guide will be mainly discussed. It will be appreciated that in any one therapy one or a number of radioactive sources may be used at one time, and the use of more than one source necessitates a like number of tubular guides 4 connected to connection head 5. Only one tubular guide 4, and hence only one "channel", is shown in FIG. 1 for clarity. A positioning member 6 is placed by a physician for the radiotherapy (as shown in more detail in FIGS. 2 and 3, discussed below) and that positioning member is connected to tubular guide 4 by way of an adaptor 7. An adaptor. 8 also connects tubular guide 4 to connection head 5.

While not shown in the drawings, such apparatus may also have a check cable, driven by check cable drive. The check cable is used to test the connections of the apparatus to the patient prior to moving the radioactive source from the safe to the patient. The check cable insures that all connections are operating properly and that the positioning members are correctly in place before the radioactive source is removed from the safe. Additionally, such apparatus may have an automatic calibration device (not shown in the drawings) for calibrating the excursion of the cable to insure that the cable has reached the correct position at the therapy site. Further, such apparatus may have an indexer for indexing the cables, especially where a plurality of cables are used for multiple radioactive source therapy. Finally, such apparatus may have an optical verification device (not shown in the drawings) for verifying that the adaptor 8 is properly connected to connection head 5. These verification devices usually consist of an electric eye which senses a portion of the adaptor 8 when that adaptor is placed in connection head 5.

FIG. 2 shows positioning members 20, which can take the form of needles, tubes, cannula or the like, placed about a breast cancer 21 by a physician. Positioning members 20 are connected to tubular guides 22 by adaptors 23 (in this illustration, three "channels" are used).

FIG. 3 shows a positioning member 30, in the form of a cannula inserted in the bronchus 31 for treating a lung cancer 32. In this embodiment, the cannula 30 may extend from the head 5 to the cancer 32 and as such the canula 30 functions as both the tubular guide and the positioning member. Hence, the cannula 30 need only have a adaptor for connecting the cannula 30 to head 5, as briefly noted above.

FIGS. 2 and 3 are simply diagrammatic illustrations of typical arrangements for radioactive therapy using a remote after-loading apparatus. However, similar arrangements can be used for treating the oesophagus, the head and neck, the oral cavity, the brain, the cervix, the endometrium, the prostate, the bladder, the bowel duct, and the nasopharynx, among others. The various arrangements for treating the various body parts varies with the particular treatment, but all of the arrangements have in common the basic parts of the remote after-loading apparatus, as described above. Thus, no further explanation of the known remote after-loading apparatus for radiotherapy need be described herein, and more details can be found in the brochure MICROSELECTRON HDR $^{192}$Ir published by Nucletron International BV, Leersum, The Netherlands, the entire disclosure of which is incorporated herein by reference. Additional disclosure may be found in the publication MICROSELECTRON LDR/MDR $^{192}$Ir $^{137}$Cs published by Nucletron Trading BV, Leersum, The Netherlands, the entire disclosure of which is incorporated herein by reference.

As noted above, a major problem in connection with the use of such apparatus has been in regard to the adaptors 7 and 8 (see FIG. 1) for connecting guide members, e.g. tubular guide 4 to the positioning member 6 and to the connection head 5. Also, as noted, typically the prior art used metal tubes for making such attachments of the guide member, e.g. tubular guide 4 to the adaptors. The guide member is quite small, especially guide members in the form of a canula for bronchus application, which canula extends from the site of therapy to the connection head 5 and such guide members are typically no more than two millimeters in diameter, with a lumen which is less than about 1.8 millimeters. As can be appreciated, using conventional adaptors, as explained above, and the like for attaching such small tubular guides to the adaptors requires fine and intricate work, and such work considerably slows down the attachment of the tubular guide to the positioning member, once the positioning member is in place in the patient, and delays attaching the tubular guide to the connection head 5 of the after-loading apparatus. When multiple "channels" are used, considerable delays are experienced. Further, in view of such small diameters, it is easy to unduly distort or compress the tubular guide with such adaptors and such distortion or compression can cause kinking or binding of the source drive cable when passing therethrough. The clearance between the lumen of the tubular guide and the source drive cable is kept small so that the source drive cable may be driven through that lumen, even in complex configurations, without kinking. The probability of such distortion or compression of the tubular guide with such conventional adaptors makes conventional adaptors a serious problem in the art of the remote after-loading apparatus.

The invention provides an adaptor which can be used for connecting the tubular guide to the connection head and the positioning member, as shown in FIG. 1, or the positioning member to the tubular guide, as shown in FIG. 2, or the tubular guide, in the form of a canula, to the connection head, as shown in FIG. 3, in a fast and efficient manner and with virtually no possibility of unduly compressing or distorting the tubular guide and thus avoids kinking or binding of the source drive cable while passing therethrough. The invention is based upon clamping the tubular guide with compressible members so that the compression of the tubular guide within those members is essentially uniform around the circumference of the tubular guide being attached. Further, the invention is based on the attachment of the tubular guide to the adaptor being made simply by inserting the tubular guide into the adaptor, with which insertion the clamping by the adaptor automatically occurs. As can be appreciated, by providing that the compressive clamping around the tubular guide is essentially uniform around the circumference thereof, no undue compression or distortion of the tubular guide will occur and the lumen of the tubular guide will remain essentially circular, as opposed to prior art adaptor means. When the lumen remains essentially circular, there is a considerably reduced risk of the source drive cable binding or kinking while being passed from the remote after-loading apparatus to the site of therapy. Also, as will be appreciated, with the clamping device being actuated simply by inserting the very small tubular guide into the adaptor, it is very easy to make connections between the tubular guide and the positioning member and the tubular guide and the connection head, once the positioning member has been placed in the patient by the physician. This allows quick and efficient use of the apparatus, and minimizes delays and discomfort to the patient.

The principle of the present adaptor is shown in FIG. 4. The adaptor has an outer barrel 40 having an opened end 41 and a connector end 42. In this embodiment, the connector end 42 is previously attached to the tubular guide 4 (see FIG. 1) and the adaptor will in turn connect to a positioning member 20 (see FIG. 2). The barrel 40 also has a centrally extending aperture 43 therein. A sleeve 44 has a first end 45, a second end 46 and a passageway 47 extending between those two ends 45 and 46. The sleeve is configured so that it may be disposed within barrel 40 (FIG. 4 is an exploded view) such that at least the first end 45 of the sleeve 44 is contained within the barrel 40.

While various modes of manufacture may be employed, for simplicity in illustrating the invention in FIG. 4, sleeve 44 is secured in barrel 40 by threads 48 of the sleeve 44 and threads 49a of barrel 40. Other modes of assembly may be used, and the modes of assembly are not critical. However, if threaded assemblies, such as that shown in FIG. 4, are used, it is preferable that the assembly be firmly affixed together, e.g. by soldering or by use of a joint compound such as LOCKTITE, so that it may not be taken apart, in order to avoid damage to the connector.

An elongated gripping means, generally, 49 is disposed through sleeve passageway 47 and extends beyond ends 45 and 46 of the sleeve 44. The gripping means has a tubular guide gripping end 50 and a tubular guide receiving end 51. A gripping body 52 extends from the gripping end 50 to the receiving end 51. A flange 53 is disposed on gripping end 50 and the diameter of the flange is greater than the diameter of the sleeve passageway 47 at the first end 45 of sleeve 44 so that the axial excursion of the gripping means 49 to the left as shown in the drawing is limited when flange 53 contacts the first end 45 of sleeve 44. A tapered outer surface 54 extends from flange 53 to a distant portion 55 on the gripping body. A uniform diameter gripping means tube bore 56 extends through the gripping means 49. There are at least two opposed slots 57 (one shown in FIG. 4) passing through the flange 53 and the gripping body 52 and these slots extend from the flange to at least a distant portion 55 of the gripping body, although preferably these slots extend therebeyond, as shown in FIG. 4 and as explained more fully hereinafter. The at least two opposed slots 57 form at least two opposed gripping portions 58 and 59 of the gripping means 49 and the gripping portions 58 and 59 are inwardly compressible when the flange 53 and the gripping portions 58 and 59 are in contact with the first end 45 of sleeve 44, so as to form a reduced diameter of the tube bore 56 of that portion of gripping means 49, and thereby forms a closed position of the gripping portions 58 and 59. The gripping portions 58 and 59, by virtue of slots 57 are also sufficiently resilient so that when the flange 53 and the gripping portions 58 and 59 are axially disposed from the first end 45 of sleeve 44 (to the right as shown in FIG. 4) that the gripping portions 58 and 59 form an opening having at least the same diameter as the tube bore 56 and thereby, also, forms the open position of gripping portions 58 and 59.

Spring means 60 are disposed between the gripping means 49 and sleeve 44 for urging flange 53 of the gripping means 49 toward the second end 46 of sleeve 44.

As noted above, the embodiment of FIGS. 4 and 5, for illustrative purposes, shows the assembly by threads, although other assemblies may be used. However, for completing the assembly shown in FIGS. 4 and 5, a guide tube collar 61 is threaded onto gripping means 49 by threads 62 on both the gripping means 49 and collar 61. The collar 61 has an aperture 63 which communicates with tube bore 56 of gripping means 49, and when assembled, tube bore 56 also communicates with barrel bore 64 of barrel 40 such that there is a continuous communication through collar 61, gripping means 49 and barrel 40. This continuous communication forms a passageway through the adaptor for the tubular guide and positioning member, through which the source drive cable 2 passes. To facilitate the insertion of the positioning member 6 (see FIGS. 1 and 5) into the adaptor, collar 61 has a taper 65 for ease of insertion thereinto.

It will also be seen that when the arrangement of FIG. 4 is in an assembled position, spring 60 will be held in place by being between sleeve 44 and gripping means 49, as well as between shoulder 66 of collar 61 and flange 67 of sleeve 44. With the spring so restrained, it will urge collar 61 axially to the left as shown in the drawings, and since collar 61 is attached to gripping means 49, gripping means 49 will likewise be urged axially to the left as shown in the drawings and cause flange 53 to seat against first end 45 of sleeve 44, thus causing the gripping portions 58, 59 to be resiliently moved radially inwardly and form a diameter less than the diameter of bore 56, i.e., the closed position thereof.

When it is desired to attach a positioning member 6, such as a cannula, to the adaptor, the end 68 thereof (see FIG. 5) is placed into taper 65 (see FIG. 4) and passed through aperture 63 of collar 61, through the receiving end 51 of the gripping means 49, and subsequently through tube bore 56 of gripping means 49 until it reaches the distant portion 55 of gripping means 49. At that point, the diameter of tube bore 56 is less than the diameter of cannula 6 and end 68 thereof will abut the reduced diameter portion of tube bore 56 (the closed position of the gripping means). However, with further movement of cannula 6, gripping means 49 is displaced against spring 60 and axially outwardly of first end 45 of sleeve 44 (to the right as shown in the drawings) and as the tapered outer surface 54 clears first end 45, gripping portions 58 and 59, no longer being compressed within first end 45, will expand to a diameter at least the same as the diameter as that of bore 56 and cannula 6. With continued movement of cannula 6, the end 68 thereof will pass through gripping means 49 and finally will abut the entrance 70 of barrel bore 64, where end 68 will come to a stop. When that occurs, spring 60 will urge gripping means 49 and flange 53 axially toward second end 46 of sleeve 44 and cause gripping portions 58, 59 to again be compressed by first end 45 of sleeve 44 around cannula 6. This will, of course, cause a gripping action by gripping portions 58, 59 on cannula 6 and lock the cannula 6 in that position. That lock will be most secure, since any movement of canula 6 to the left, as shown in the drawings, will cause gripping portions 58, 59 to be further compressed by first end 45 and will cause further gripping and locking of cannula 6 in that position.

Thus, the canula may be moved into the receiving end 51 of the gripping means 49 and moved to an engagement with the gripping portions 58, 59 which are in the closed position. Further movement of cannula 6 causes the gripping means to be moved against spring means 60 axially outwardly from the first end 45 of sleeve 44 to a position where at least a portion of the tapered outer surface 54 is spaced from the first end 45 of sleeve 44 and the flange 5 and gripping portions 58, 59 are resiliently moved to an open position. This allows passage of cannula 6 therethrough and upon ceasing the movement of cannula 6, the spring means 60 urges the gripping means 49 and flange 53 axially inwardly in sleeve 44 so that a portion of the tapered outer surface 54 contacts first end 45 of sleeve 44 and compresses the gripping portions 58, 59 to a locked or closed position around cannula 6.

The present adaptor can be further understood from FIG. 6 which is a similar to the embodiment of FIG. 4 but shows certain components in more detail and shows a preferred embodiment of the invention. As opposed to barrel aperture 43 in FIG. 4, as shown in FIG. 6, barrel 80 has an aperture 81 that ends in an abutment 82 in substantially the same configuration as that of flange 83. Thus, flange 83, when moving to the right as shown in the drawing (when canula 6—not shown in FIG. 6—is being passed therethrough) will contact abutment 82 so that flange 83 can move no further axially out of barrel 80 (to the right as shown in the drawing) and, likewise, no further axial movement (to the right as shown in the drawing) of the gripping means 84 (shown in side view—not in section) is achievable. This configuration provides a positive and very precisely determined stop for the gripping means 84. Also, it will be noted that abutment 82 has an axially disposed abutment aperture 85 therein which has a diameter equal to that of the tube bore (or cannula 6) for passing cannula 6 therethrough. Abutment aperture 85 has a second abutment 86, the shoulders of which are less than the diameter of cannula 6, so that when the cannula 6 contacts second abutment 86, it comes to a positive stop. Therefore, the exact position of the cannula 6 can be determined from the present adaptor. Further apertures 87 and 88 complete the communication through the adaptor. Preferably, abutment aperture 85 has a centering taper 89 so as to center cannula 6 as it passes therethrough. As noted, the abutment aperture 86 is in communication with cannula 6 which is in turn in communication with a conventional coupling 90 which can be attached to various devices, such as a tubular guide as described above.

The embodiment of FIG. 6 differs from the embodiment of FIG. 4, also, in that spring 91 is restrained within sleeve 92 and a recess 93 which cooperates with collar 94. Also, there is a tapered portion 95 adjacent the first end 96 of sleeve 92 (the taper is shown in FIG. 4 but is not discussed in connection therewith). That tapered portion 95 is of the same taper configuration as the tapered outer surface 97 of gripping means 84. This allows a more positive opening and closing of opposed gripping portions 98 for a more positive release and locking of the tubular guide. Preferably, the spring means 60, in FIG. 4, and 91 in FIG. 6, is a coiled spring, although other spring arrangements may be used, and more preferably, the coiled springs surrounds the gripping means, as shown in FIGS. 4 and 6.

Also, in FIG. 6, collar 94 has a centering taper 100, similar to the taper 65 in FIG. 4, so that the receiving end of the gripping means can be easily contacted with a positioning member 6, such as a cannula, when being inserted thereinto.

The tapered outer surfaces 54 and 97 of the gripping means 49 and 84 are shown in FIGS. 4, 5 and 6 as straight tapers. However, in lieu thereof curved tapers may be used, but straight tapers are preferred. Also, while, of course, there must be at least two opposed slots 57 and 99 in gripping means 49 and 84 (see FIGS. 4 and 6), so as to provide at least two opposed gripping portions 50 and 98, preferably, there are at least three such slots and, corresponding three gripping portions. More preferably, the slots are at 120° apart and the gripping portions are of equal size. However, a better and more positive gripping action can be achieved, with even less tendency to compress or distort the tubular guide, when there are at least four slots and four opposed gripping portions, and particularly, when the slots are 90° apart and the gripping portions are of equal size. Further, to achieve the best gripping action of the gripping means, the slots extend to at least onequarter of the length of the gripping body and more preferably the slots extend to at least one-half the length of the gripping body. Likewise, to insure reasonable gripping of the cannula 6, the distant portions 55 and 101 of the gripping body 52 and 84 (see FIGS. 4 and 6) to which the tapers extend is a distance from the flange which is at least equal to the diameter of the gripping means bore, and, more preferably, at least twice that diameter.

Figure 7:
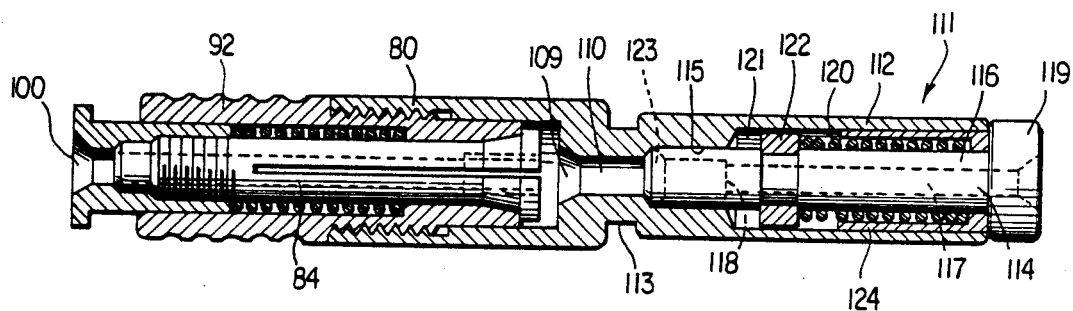
FIG. 7 is a view of a further preferred embodiment of the present adaptor, having an indicator connected therewith, and that view is partially in cross section.

The embodiment shown in FIG. 7 is similar to that shown in FIG. 6, with the major exception that the embodiment of FIG. 7 also has associated therewith an indicator means and may be used to connect either a tubular guide or a cannula to head 5 (see FIG. 1). In FIG. 7 the abutment aperture 109 connects with an indicator aperture 110 in indicator means, generally, 111. The indicator means has an indicator housing 112 with a connection end 113, usually in the shape of a groove or sleeve, and an indicator end 114. Axially positioned in housing 112 is a housing aperture 115 which housing aperture connects with the indicator aperture 110. An indicator body 116 is disposed within housing 112 and within the housing aperture 115. Indicator body 116 connects indicator end 114 and connection end 113. An indicator bore 117 passes through the indicator body with a portion of the indicator bore 117 which is within the indicator aperture 110 having the same diameter as the diameter of the tube bore of gripping means 84 and the remainder of the indicator bore 117 having a reduced bore 118 of a diameter which is less than the diameter of the tube bore of gripping means 84 so that the tubular guide or cannula may be moved through the adaptor and into the indicator means to a position where the tubular guide or cannula contacts the reduced diameter 118 of the indicator bore 117.

An indicator flange 119 is disposed at the indicator end 114 of the indicator body 116 and that flange has a diameter greater than the diameter of housing aperture 115. A spring means 120 is disposed between the housing 112 and the indicator body 116 and held in place by recess 121, collar 122 and sleeve 124, for urging the indicator body toward abutment aperture 109. Thus, when a tubular guide 4 (see FIG. 1) or a cannula 30 (see FIG. 3) is passed through taper 100, gripping means 84, indicator aperture 110 and abuts reduced diameter 118 of indicator bore 117, with further movement of the cannula or tubular guide toward the indicator end 114 of the housing 112, the indicator flange 119 is displaced (to the right as shown in the drawing) from the housing 112 and protruded from indicator end 114, which protrusion provides an indication that the cannula or tubular guide has reached the reduced diameter 118 of indicator bore 117. Preferably, the end of the indicator bore 117 which connects the abutment aperture 109 has a centering taper 123, to assure smooth transition from the adaptor to the indicator by the tubular guide.

The connection head 5 (FIG. 1) has a photocell device therein (not shown) which is actuated when flange 119 is moved axially outwardly of the indicator housing 112 (to the right shown in the drawing) which is a positive indicator that the adaptor is properly in place in connection head 5.

As can therefore be seen, a cannula or tubular guide can be inserted into the adaptor at centering taper 100, passed through the gripping means 84, and into the indicator means 111 until it abuts reduced diameter 118. The gripping action on the cannula or tubular guide will be the same as described in connection with FIGS. 4, 5 and 6, but in addition thereto, by further movement of the cannula or tubular guide against reduced diameter 118, flange 119 will be moved outwardly of housing 112 (to the right as shown in the drawing) and cause actuation of the photocell device in head 5. Thus, the combination shown in FIG. 7 not only grips the cannula or tubular guide, in the manner described in FIGS. 4, 5 and 6, but also provides a positive indication that the adaptor (with the indicator means of FIG. 7) is correctly in place in connection head 5.

When the after-loading apparatus, including the positioning members, tubular guide, etc. are in place, the technician activates the drive cable to move the radioactive source to the site of the therapy. After sufficient exposure, for the particular treatment involved, of the radioactive source to the tissue being treated, the technician again activates the drive cable to remove the drive cable and the radioactive source back into the safe for the radioactive source. This is all done while the technician is not in close proximity to the patient being treated, e.g. in another room, in order to avoid radiation exposure by the technician. At this time, it is important for the comfort of the patient to also quickly disconnect the after-loading apparatus from positioning members, such as positioning members 20 (see FIG. 2), from the patient, so that the patient can comfortably move or to quickly disconnect the tubular guides from the apparatus. With the present invention such disconnecting is easily achieved. In this regard, and for all of the embodiments discussed above, the positioning member or tubular guide is disconnected from the adaptor (or the adaptor-indicator combination) simply by digitally pressing collar 61 axially inwardly (see FIG. 4) against spring 60 or pressing collar 94 against spring 91 (FIG. 6) so as to move the gripping means 49 or 84 axially inwardly of the adaptor (to the right as shown on the drawings), which will of course allow flange 53 (see FIG. 4) or flange 83 (see FIG. 6) to be displaced to the opened position as discussed above. When in that open position, the tubular guide of the positioning member may simply be pulled from the adaptor (or from the adaptor-indicator combination—see FIG. 7) in one smooth easy movement. Thus, no manual removal of tubes or unscrewing of an adaptor and the like are required, and the time for disconnecting the tubular guide or the positioning member from the patient or the tubular guide from the apparatus with the present invention is far reduced from the time required with conventional adaptors, especially when multiple channels are used.

Thus, the invention provides adaptors for remote after-loading apparatus which are quick and easy to connect to the positioning member or tubular guide, which insure that these will not be compressed or distorted to cause binding of the drive cables, and which are quick and easy to disconnect once the therapy has been completed. This is a substantial improvement in the art and greatly facilitates the use of remote after-loading apparatus both in terms of accuracy of application of the radioactive source and comfort to the patient. A most important feature of the invention is the design of the present gripping means which will automatically grip the positioning member or tubular guide as it is passed therethrough and will also allow quick and easy disconnecting thereof after the therapy has been completed. Another important feature of the invention is the design wherein the abutment of the positioning member or tubular guide in the adaptor positively places the same for indexing the length of cable to be driven by the cable drive of the remote after-loading apparatus. Finally, an important feature of the invention is the indicator means for positively indicating that the tubular guide or positioning member is fully in place in the adaptor and the adaptor is fully in place in the head when the adaptor is used for connecting the tubular guide or the positioning member to the head of the remote after-loading apparatus. All of these features are most important and are substantial improvements in the art.

We claim:

1. In a remote, after-loading apparatus for brachy radiotherapy comprising a radioactive source, a safe for the source, a source drive cable, a guide member for guiding the cable to the site of radiotherapy, a connection head for connecting the guide member to the source drive cable, a positioning member for positioning the source at the site of the radiotherapy and adaptors for connecting the guide member to the connection head and/or to the positioning member, the improvement wherein at least one of the said adapters comprises:

(1) an outer barrel having an opened end and a connector end and having a centrally extending barrel aperture therein;

(2) a sleeve having a first end and a second end and a sleeve passageway extending between said ends, and the first end of a sleeve being disposed within the opened end of said barrel such that at least the first end of the sleeve is contained within said barrel;

(3) an elongated gripping means disposed through said sleeve passageway and extending beyond the ends of the said sleeve, said gripping means having:

(a) a gripping end disposed near the first end of said sleeve and a receiving end disposed near the second end of said sleeve;

(b) a gripping body extending from said gripping end to said receiving end;

(c) a flange disposed on said gripping end where the diameter of the flange is greater than a diameter of said sleeve passageway at the first end thereof;

(d) a tapered outer surface extending from said flange to a distant portion of said gripping body;

(e) a uniform diameter gripping means tube bore extending through said gripping means;

(f) at least two opposed slots passing through said flange end and said gripping body and extending from said flange to at least said distant portion of said gripping body;

(g) said at least two slots forming at least two opposed gripping portions of said gripping means and said gripping portions being inwardly compressible when the said flange and gripping portions are in contact with the said first end of the sleeve so as to form a reduced diameter of said tube bore and thereby a closed position of the gripping portions, and said gripping portions being sufficiently resilient so that when the said flange and gripping portions are axially disposed from the said first end of the sleeve the gripping portions form at least the same diameter as the tube bore and thereby an open position;

(4) spring means disposed between said gripping means and said sleeve for urging the said flange on the gripping means toward the said second end of the sleeve;

whereby the guide member may be moved into the receiving end of the gripping means, moved to an engagement with the said gripping portions in the said closed position, moved so as to cause the gripping means to be moved against said spring means axially outwardly from the first end of the said sleeve to a position where at least a portion of said tapered outer surface is spaced from the said first end of the sleeve and the flange and gripping portions are resiliently moved to said open position and allow passage of the guide member therethrough, and upon ceasing the movement of the guide member, the spring means urges the gripping means axially inwardly in the said sleeve so that a portion of the said tapered outer surface contacts the said first end of the sleeve and compresses the said gripping portions to a locked position around said guide member.

2. The apparatus of claim 1 wherein the said barrel aperture has an abutment in substantially the same configuration as that of said flange so that when the flange contacts the said abutment no further axial movement of said gripping means is achievable.

3. The apparatus of claim 2 wherein the abutment has an axially disposed abutment aperture therein which has a diameter substantially equal to that of the said tube bore for passing the said guide member therethrough.

4. The apparatus of claim 3 wherein the said abutment aperture has a centering taper.

5. The apparatus of claim 3 wherein the said abutment aperture connects with an indicator aperture in an indicator means, said indicator means having:
   (a) an indicator housing with a connection end, an indicator end and an axially positioned housing aperture which housing aperture connects with said indicator aperture;
   (b) an indicator body disposed within said housing and within said indicator aperture and said indicator body connecting said connection end and said indicator end;
   (c) an indicator bore passes through said indicator body with a portion of the indicator bore which is within the indicator aperture having the same diameter as the said gripping means tube bore and the remainder of the indicator bore having a reduced bore of a diameter which is less than the diameter of the said gripping means tube bore, whereby the said guide member may be moved through said adaptor, and into said indicator means to a position where said guide member contact said reduced bore;
   (d) an indicator flange disposed of the indicator end of the indicator body, said flange having a diameter greater than the diameter of the housing aperture;
   (e) spring means disposed between said housing and said indicator body for urging the indicator body towards said abutment aperture;
whereby when said guide member abuts the said reduced diameter and when the said guide member is axially moved toward said indicator end of the housing, the indicator flange is displaced from the housing and provides an indication that the said guide member has reached the said reduced diameter.

6. The apparatus of claim 5 wherein the end of the said indicator bore which connects with the said abutment aperture has a centering taper.

7. The apparatus of claim 1 wherein the said sleeve passageway has a tapered portion adjacent said first end and wherein the said tapered portion is of the same taper configuration as the tapered outer surface of the gripping means.

8. The apparatus of claim 1 wherein there is a recess in the sleeve passageway and the said spring means is disposed in the recess and held therein by the recess and the outer surface of the gripping means.

9. The apparatus of claim 8 wherein the spring means is a coiled spring.

10. The apparatus of claim 9 wherein the coiled spring surrounds the gripping means.

11. The apparatus of claim 1 wherein the tube receiving end of the gripping means has a centering taper surrounding said gripping means tube bore.

12. The apparatus of claim 1 wherein the said flange has a diameter slightly less than a diameter of the said barrel aperture 13. The apparatus of claim 1 wherein the said tapered outer surface of the gripping means is a straight or curved taper.

14. The apparatus of claim 13 wherein the said taper is a straight taper.

15. The apparatus of claim 1 wherein there are three slots and three gripping portions.

16. The apparatus of claim 15 wherein the slots are 120° apart and the gripping portions are of equal size.

17. The apparatus of claim 1 wherein there are four slots and four gripping portions.

18. The apparatus of claim 17 wherein the slots are 90° apart and the gripping portions are of equal size.

19. The apparatus of claim 1 wherein the slots extend to at least one-quarter of the length of the gripping body.

20. The apparatus of claim 19 wherein the slots extend to at least one-half the length of the gripping body.

21. The apparatus of claim 1 wherein the said distant portion of the gripping body to which the said taper extends is a distance from the flange which is at least equal to the diameter of the gripping means bore.

22. The apparatus of claim 21 wherein the said distance is at least equal to or twice the diameter of the gripping means bore.

* * * * *